Jan. 19, 1971 A. K. MANBECK Plant Pat. 3,021
LINDEN TREE
Filed April 18, 1969 2 Sheets-Sheet 1
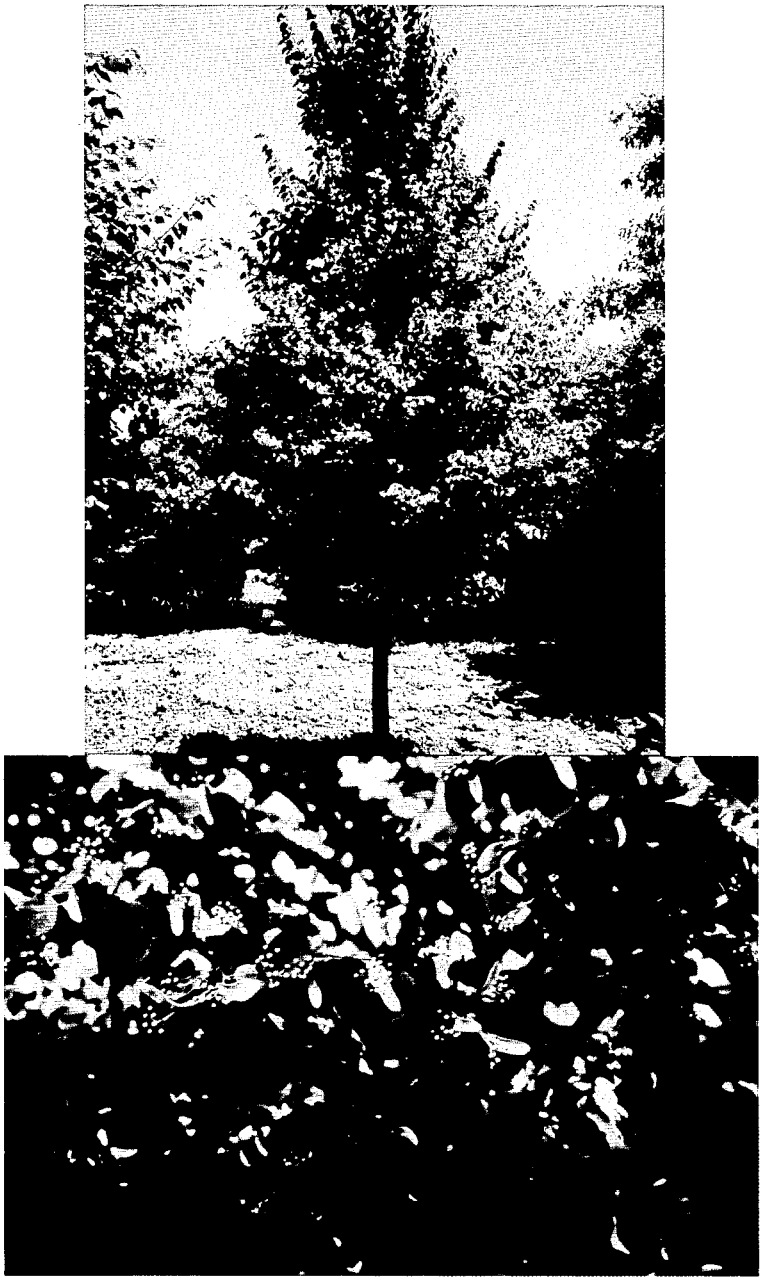
Inventor.
Alton K. Manbeck
By: Robb & Robb
Attorneys.

LINDEN TREE
Filed April 18, 1969 2 Sheets-Sheet 2
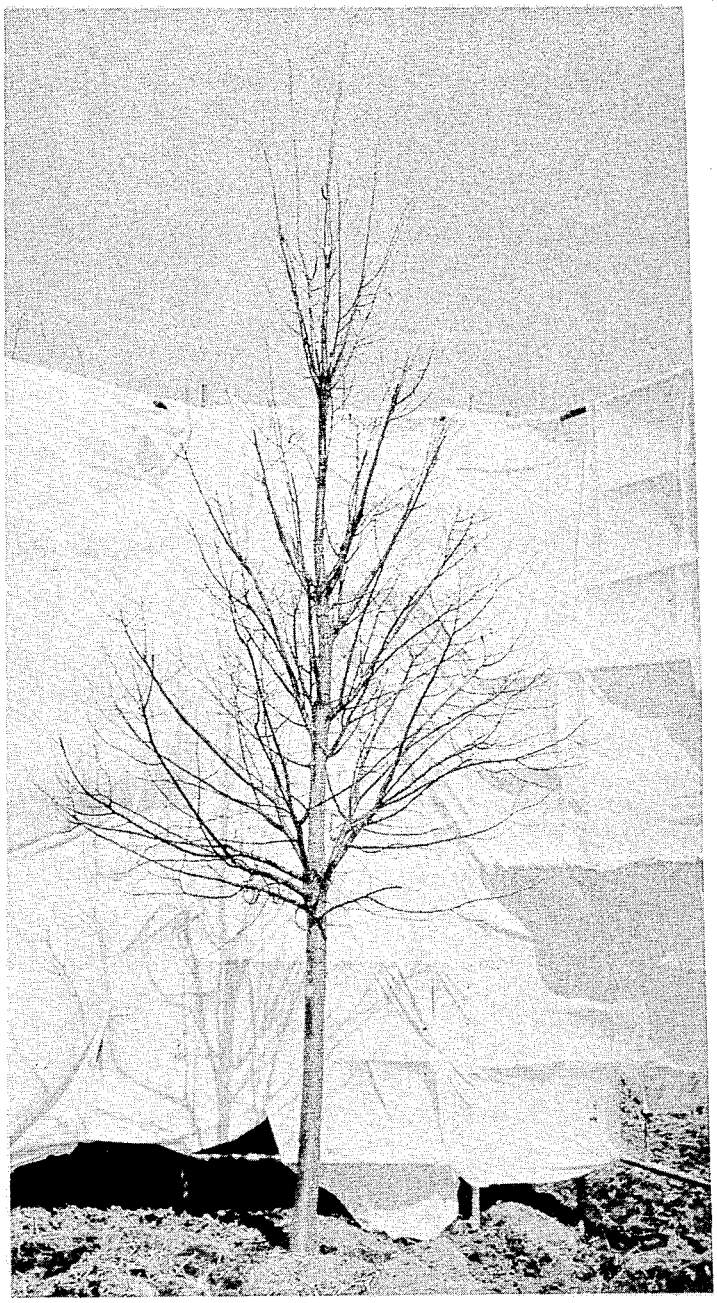
Inventor.
Alton K. Manbeck
By: Robb & Robb
Attorneys.

United States Patent Office

Plant Pat. 3,021
Patented Jan. 19, 1971

3,021
LINDEN TREE

Alton K. Manbeck, New Knoxville, Ohio, assignor to A. K. Manbeck & Sons Nurseries, Inc., New Knoxville, Ohio, a corporation of Ohio Filed Apr. 18, 1969, Ser. No. 817,584
Int. Cl. A01h 5/12
U.S. Cl. Plt.—51 1 Claim The present invention relates to a new and distinct variety of linden tree which was discovered by me on my cultivated nursery property located at New Knoxville, Ohio, as a newly found seedling of unknown parentage, but apparently being a mutation of an unidentified variety of the linder species botanically known as *Tilia cordata.*

At the time of my discovery, I was growing in my nursery aforesaid a block of linden seedlings of the *Tilia cordata* species which I had acquired from an Oregon nursery. In the course of my care and cultivation of these seedlings, my attention was attracted to one particular tree in the block which was significantly different from all others in that it distinctly showed a more abundant blooming habit, bearing from 3 to 4 times as many blooms as any other trees in the same block. I thereupon promptly took steps to carefully preserve this seedling and to keep it under close observation. Continued observations of the original seedling and progeny thereof reproduced therefrom by budding, as performed on my behalf at Fairview, Oreg., and by me in my nursery at New Knoxville, Ohio, have fully confirmed the more abundant blooming habit than the normal blooming habit of *Tilia cordata* seedlings. In addition, I have found that the new seedling is more pyramidal in its habit of growth, with a semi-horizontal and very even branching habit around the leader of the tree, and the tree bears foliage that is smaller in size and glossier in appearance than the normal foilage of varieties of the *Tilia cordata* species. From my continued observations over a prolonged period of years, I am convinced that although the specific parentage of my new seedling is not definitely known, it represents a new and improved variety of distinct commercial value, and that it is distinguished from the normal *Tilia cordata* species, as well as from all other varieties of linder trees of which I am aware.

The accompanying drawing shows in black and white a typical dormant tree, without foliage, of my new variety which is illustrative of its distinctive habit of growth, and also shows in color a typical specimen tree in the blooming stage and typical specimens of the foliage and flowers on a somewhat enlarged scale.

The following is a detailed description of the new variety, with color terminology in accordance with Maerz & Paul Dictionary of Color, except where general color terms of ordinary dictionary significance are obvious:

Parentage: Newly found seedling of an unidentified variety of *Tilia cordata.*

Propagation: Holds its distinguishing characteristics through succeeding propagations by budding.

Tree: Medium size; pyramidal shape; dense; hardy.

*Trunk.*—Smooth. Color: Autumn, Plate 8, 12A, page 39.

*Branches.*—Smooth. Color: Same as trunk color.

*Lenticels.*—Normal.

*Leaves.*—Quantity; Normal. Size: Small; average from 3 to 5 cm. wide, and from 2 to 5 cm. long; a substantial percentage are wider than length. Shape: Normal except for small size. Color: Dark green, but glossier than the normal leaves of *Tilia cordata*; under surface glaucous; upper surface—Swamp Green, Plate 24, 9E, page 71; under surface—Palmetto Green, Plate 22, 6B, page 67. Margin: Finely serrate. Petiole: Medium length (from 1 to 2 cm.); slender. Glands: Normal number; opposite; normal size; slightly globose.

Flower buds:

*Hardiness.*—Average for species.

*Arrangement.*—From 5 to 7 in pendants.

*Shape.*—Globose.

*Color.*—Yellowish creamy white.

Flowers: Same as typical of the species *Tilia cordata.*

*Dates of first and full bloom.*—Averages about May 20 and May 25, respectively.

*Quantity.*—Very abundant.

*Size.*—Medium.

*Borne.*—In pendants of from 5 to 7 or more on nearly upright cymes, with glabrous floral bracts ranging from about 3.5 to 8 cm. long.

*Color.*—Marguerite Yellow, Plate 10, 1C, page 43, and when viewed from a distance, the tree resembles a flowering crab because of profusion of bloom.

*Stamens.*—Length about equal to petal length.

*Fragrance.*—Very strong.

Fruit: Globose; smooth; thin walled.

I claim:

1. A new and distinct variety of linden tree, substantially as herein shown and described, characterized particularly as to novelty by its general similarity to the species botanically known as *Tilia cordata,* but being distinguished from varieties typical of said species by the unique combination of a substantially pyramidal habit of growth, with a semi-horizontal and a very even branching habit around the leader of the tree, leaves of smaller size and a more glossy appearance than those typical of the aforementioned species, and a more abundant blooming habit ranging from 3 to 4 times as many blooms as is typical for said species, giving the tree and appearance resembling a flowering crab when viewed from a distance.

No references cited.

ROBERT E. BAGWILL, Primary Examiner